(12) United States Patent
Brenneman

(10) Patent No.: US 9,706,997 B2
(45) Date of Patent: *Jul. 18, 2017

(54) DEVICE AND METHOD FOR ESTABLISHING AN ARTIFICIAL ARTERIO-VENOUS FISTULA

(75) Inventor: Rodney A. Brenneman, San Juan Capistrano, CA (US)

(73) Assignee: ROX Medical, Inc., San Clemente, CA (US)

( * ) Notice: Subject to any disclaimer, the term of this patent is extended or adjusted under 35 U.S.C. 154(b) by 1381 days.

This patent is subject to a terminal disclaimer.

(21) Appl. No.: 11/356,876

(22) Filed: Feb. 17, 2006

(65) Prior Publication Data

US 2006/0206123 A1    Sep. 14, 2006

Related U.S. Application Data

(63) Continuation-in-part of application No. 10/927,704, filed on Aug. 27, 2004, now abandoned.

(51) Int. Cl.
| | | |
|---|---|---|
| *A61F 2/06* | (2013.01) | |
| *A61B 17/11* | (2006.01) | |
| *A61B 17/08* | (2006.01) | |
| *C09K 8/508* | (2006.01) | |
| *C09K 8/518* | (2006.01) | |

(Continued)

(52) U.S. Cl.
CPC ............ *A61B 17/11* (2013.01); *A61B 17/083* (2013.01); *C09K 8/5083* (2013.01); *C09K 8/518* (2013.01); *C09K 8/5753* (2013.01); *C09K 8/62* (2013.01); *C09K 8/68* (2013.01); *A61B 17/10* (2013.01); *A61B 2017/00243* (2013.01); *A61B 2017/00862* (2013.01); *A61B 2017/00867* (2013.01);

(Continued)

(58) Field of Classification Search
CPC .................. A61B 17/083; A61B 17/11; A61B 2017/1103; A61B 2017/1107; A61B 2017/1117; A61B 2017/1132; A61B 2017/1135; A61B 2017/1139; A61B 2017/00252; A61B 17/1114; A61B 17/1128; A61B 17/115; A61B 17/1152; A61B 2017/1157; A61F 2/064; A61F 2002/821; A61M 27/002
USPC .............. 623/1.36, 1.13, 1.15; 606/153–156; 604/8
See application file for complete search history.

(56) References Cited

U.S. PATENT DOCUMENTS

| | | |
|---|---|---|
| 3,538,917 A | 11/1970 | Selker |
| 3,675,656 A | 7/1972 | Hakim |

(Continued)

FOREIGN PATENT DOCUMENTS

| | | |
|---|---|---|
| EP | 1614400 A2 | 1/2006 |
| EP | 1470785 A1 | 10/2007 |

(Continued)

OTHER PUBLICATIONS

"Causes of Erectile Dysfunction", eMedicine Health website, http://www.emedicinehealth.com/causes_of_erectile_dysfunction/page3_em.htm.

(Continued)

*Primary Examiner* — Darwin Erezo
*Assistant Examiner* — Lindsey Bachman
(74) *Attorney, Agent, or Firm* — Levine Bagade Han LLP

(57) ABSTRACT

A shunt rivet for implantation in the aorta and inferior vena cava to treat chronic obstructive pulmonary disease, and a method of treating chronic obstructive pulmonary disease.

24 Claims, 8 Drawing Sheets

(51) Int. Cl.
 *C09K 8/575* (2006.01)
 *C09K 8/62* (2006.01)
 *C09K 8/68* (2006.01)
 *A61B 17/10* (2006.01)
 *A61B 17/00* (2006.01)

(52) U.S. Cl.
 CPC ............... A61B 2017/1107 (2013.01); A61B 2017/1139 (2013.01)

(56) References Cited

U.S. PATENT DOCUMENTS

| | | | |
|---|---|---|---|
| 3,730,186 A | 5/1973 | Edmunds, Jr. et al. | |
| 3,882,862 A | 5/1975 | Berend | |
| 4,586,501 A | 5/1986 | Claracq | |
| 4,601,718 A | 7/1986 | Possis et al. | |
| 4,828,544 A | 5/1989 | Lane et al. | |
| 5,108,420 A | 4/1992 | Marks | |
| 5,258,042 A | 11/1993 | Mehta | |
| 5,491,224 A | 2/1996 | Bittner et al. | |
| 5,507,725 A | 4/1996 | Savage et al. | |
| 5,756,696 A | 5/1998 | Gray et al. | |
| 5,830,222 A | 11/1998 | Makower | |
| 5,830,224 A | 11/1998 | Cohn et al. | |
| 5,843,170 A | 12/1998 | Ahn | |
| 5,944,738 A | 8/1999 | Amplatz et al. | |
| 6,053,891 A | 4/2000 | DeCampli | |
| 6,099,542 A | 8/2000 | Cohn et al. | |
| 6,113,612 A | 9/2000 | Swanson et al. | |
| 6,120,534 A | 9/2000 | Ruiz | |
| 6,152,937 A * | 11/2000 | Peterson et al. | 606/153 |
| 6,168,620 B1 | 1/2001 | Kerr | |
| 6,174,681 B1 | 1/2001 | Halling et al. | |
| 6,193,734 B1 | 2/2001 | Bolduc et al. | |
| 6,231,587 B1 | 5/2001 | Makower | |
| 6,309,415 B1 | 10/2001 | Pulnev et al. | |
| 6,376,188 B1 | 4/2002 | Halling et al. | |
| 6,391,036 B1 | 5/2002 | Berg et al. | |
| 6,451,048 B1 | 9/2002 | Berg et al. | |
| 6,494,889 B1 | 12/2002 | Fleischman et al. | |
| 6,579,311 B1 | 6/2003 | Makower | |
| 6,599,303 B1 | 7/2003 | Peterson et al. | |
| 6,616,675 B1 | 9/2003 | Evard et al. | 606/155 |
| 6,626,920 B2 | 9/2003 | Whayne | |
| 6,669,709 B1 | 12/2003 | Cohn et al. | |
| 6,695,878 B2 | 2/2004 | McGuckin, Jr. et al. | |
| 6,699,256 B1 * | 3/2004 | Logan | A61B 17/11 606/153 |
| 6,702,828 B2 | 3/2004 | Whayne | |
| 6,746,426 B1 | 6/2004 | Flaherty et al. | |
| 6,746,464 B1 | 6/2004 | Makower et al. | 606/185 |
| 6,797,083 B2 | 9/2004 | Peterson | |
| 6,858,035 B2 | 2/2005 | Whayne | |
| 6,913,607 B2 | 7/2005 | Ainsworth et al. | |
| 6,926,690 B2 | 8/2005 | Renati | |
| 6,972,023 B2 | 12/2005 | Whayne et al. | |
| 6,979,351 B2 | 12/2005 | Forsell et al. | |
| 7,011,094 B2 | 3/2006 | Rapacki et al. | |
| 7,056,326 B2 * | 6/2006 | Bolduc et al. | 606/153 |
| 7,175,644 B2 | 2/2007 | Cooper et al. | |
| 7,182,771 B1 | 2/2007 | Houser et al. | |
| 7,303,569 B2 | 12/2007 | Yencho et al. | |
| 7,316,706 B2 | 1/2008 | Bloom et al. | |
| 7,351,247 B2 | 4/2008 | Kupiecki et al. | |
| 7,361,181 B2 | 4/2008 | Hindrichs et al. | |
| 7,462,162 B2 | 12/2008 | Phan et al. | |
| 7,780,686 B2 | 8/2010 | Park et al. | |
| 8,273,095 B2 | 9/2012 | Brenneman et al. | |
| 2002/0165561 A1 | 11/2002 | Ainsworth | |
| 2002/0169466 A1 | 11/2002 | Peterson | |
| 2002/0189727 A1 | 12/2002 | Peterson | |
| 2003/0088256 A1 | 5/2003 | Conston et al. | |
| 2003/0100920 A1 | 5/2003 | Akin et al. | |
| 2003/0187499 A1 | 10/2003 | Swanson et al. | |
| 2004/0087997 A1 | 5/2004 | Brenneman | |
| 2004/0211433 A1 | 10/2004 | Albright | |
| 2004/0220598 A1 | 11/2004 | Bolduc et al. | |
| 2004/0249334 A1 | 12/2004 | Cull | |
| 2004/0249335 A1 | 12/2004 | Faul et al. | 604/8 |
| 2005/0049675 A1 | 3/2005 | Wallace | |
| 2005/0060041 A1 * | 3/2005 | Phan et al. | 623/23.7 |
| 2005/0065589 A1 * | 3/2005 | Schneider et al. | 607/126 |
| 2005/0107733 A1 | 5/2005 | Faul et al. | |
| 2005/0124892 A1 | 6/2005 | Weitzel et al. | |
| 2005/0228402 A1 | 10/2005 | Hofmann | |
| 2006/0047337 A1 | 3/2006 | Brenneman | |
| 2006/0129083 A1 | 6/2006 | Brenneman et al. | |
| 2006/0293701 A1 | 12/2006 | Ainsworth et al. | |
| 2007/0173867 A1 | 7/2007 | Brenneman | |
| 2007/0249985 A1 | 10/2007 | Brenneman et al. | |
| 2011/0092877 A1 | 4/2011 | Brenneman | |
| 2012/0101423 A1 | 4/2012 | Brenneman | |

FOREIGN PATENT DOCUMENTS

| | | |
|---|---|---|
| JP | 01-286478 | 10/2001 |
| WO | WO 97/13471 | 4/1997 |
| WO | WO 01/05463 | 1/2001 |
| WO | WO 01/72367 | 10/2001 |
| WO | WO 02/091952 | 11/2002 |
| WO | WO 2004/087236 | 10/2004 |
| WO | WO 2006/026279 A2 | 3/2006 |
| WO | WO 2006/066210 A2 | 6/2006 |
| WO | WO 2006/121855 | 11/2006 |
| WO | WO 2007/005386 A1 | 1/2007 |
| WO | WO 2007/014283 A2 | 2/2007 |

OTHER PUBLICATIONS

"Chronic Obstructive Pulmonary Disease (COPD) Fact Sheet (Chronic Bronchitis and Emphysema)", Feb. 16, 2007, American Lung Association website, www.lungusa.org/site/pp.asp?e=dvLUK9O0E&b=35020.

"COPD: How is COPD Treated?", Feb. 16, 2007, National Heart Lung and Blood Institute Diseases and Conditions Index website, www.nhlbi.nih.gov/health/dci/Diseases/Copd/Copd_Treatments.html.

"Lung—Treatment of COPD and Asthma", Feb. 16, 2007, NLHEP website, www.nlhep.org/lung.trtmnt.html.

Ruebben et al., "Arteriovenous fistulas induced by femoral arterial catheterization: percuntaneous treatment," *Radiology*, 209:729, 1998.

Schlensak et al., "Pulmonary Artery Banding with a Novel Percuntaneously, Bidirectionally Adjustable Device," *Eur. J. of Cardio-thoracic Surg.*, pp. 931-933, 1997.

U.S. Appl. No. 11/696,635, filed Apr. 4, 2007 in the name of Brenneman et al., Notice of Allowance mailed Sep. 21, 2010.

Australian Application No. 2005280230 filed Aug. 23, 2005 in the name of Brenneman, Office Action mailed Mar. 23, 2010.

European Application No, 05792569.5 filed Aug. 23, 2005 in the name of ROX Medical, Inc., Office Action mailed Jun. 2, 2010.

European Application No. 05792569.5 filed Aug. 23, 2005 in the name of ROX Medical, Inc., Supplement European Search Report mailed Feb. 4, 2010.

U.S. Appl. No. 10/927,704, filed Aug. 27, 2004 in the name of Brenneman, Non-final Office Action mailed Nov. 12, 2009.

U.S. Appl. No. 11/562,940, filed Nov. 22, 2006 in the name of Brenneman et al., Non-final Office Action mailed May 11, 2010.

U.S. Appl. No. 11/696,635, filed Apr. 4, 2007 in the name of Brenneman et al., Final Office Action mailed Sep. 1, 2009.

U.S. Appl. No. 11/696,635, filed Apr. 4, 2007 in the name of Brenneman et al., Notice of Allowance mailed Apr. 21, 2010.

PCT International Patent Application No. PCT/US2006/030031 filed Aug. 23, 2005 in the name of ROX Medical, Inc., International Search Report mailed Jul. 1, 2008.

PCT International Patent Application No. PCT/US2007/061986 filed Feb. 12, 2007 in the name of ROX Medical, Inc., International Search Report mailed Nov. 14. 2007.

(56) References Cited

OTHER PUBLICATIONS

PCT International Patent Application No. PCT/US2008/058315 filed Mar. 26, 2008 in the name of ROX Medical, Inc., International Search Report mailed Aug. 15, 2008.

* cited by examiner

DEVICE AND METHOD FOR ESTABLISHING AN ARTIFICIAL ARTERIO-VENOUS FISTULA

This application is a continuation-in-part of U.S. application Ser. No. 10/927,704 filed Aug. 27, 2004, now abandoned.

FIELD OF THE INVENTIONS

The inventions described below relate to treatments for pulmonary hypertension and vascular surgery.

BACKGROUND OF THE INVENTIONS

Chronic obstructive pulmonary disease (COPD), chronic hypoxia, hypertension, and left ventricular hypertrophy and pulmonary hypertension are diseases of the cardiopulmonary system. Chronic obstructive pulmonary disease (COPD), which includes chronic bronchitis and emphysema, is a slowly progressive lung disease caused primarily by smoking. In COPD, the lungs are damaged and the airways are partly obstructed, making it difficult to breath and leading to a gradual loss of lung function. Symptoms of COPD include chronic cough, excessive sputum production, low blood oxygen levels and severe disabling shortness of breath. COPD represents the fourth leading cause of death in the United States. Chronic hypoxia (reduction of oxygen supply to the body despite adequate blood flow through the body), hypertension, and left ventricular hypertrophy are related conditions which may be symptomatic of COPD or coincident with COPD.

These serious conditions affect many people, and the primary treatments are merely ameliorative. The primary treatments for COPD include avoidance of irritants such as tobacco smoke and breathing supplemental oxygen. In advanced cases of COPD, lung reduction surgery is sometimes performed, but it is not clear that it helps. There is no known cure for COPD.

An aortocaval fistula (ACF) is a rare clinical condition that can be either spontaneous (80% of the cases), related to abdominal aortic aneurysm, or the result of some trauma such as lumbar disk surgery. It is currently seen as a defect that should be cured with surgery and, possibly, stent-graft implantation in the aorta.

Contrary to this understanding, an intentionally formed aortocaval fistula appears to be a viable treatment for COPD. Recently, in our co-pending U.S. patent application Ser. No. 10/820,169 filed Apr. 6, 2004, entitled *Implantable Arteriovenous Shunt Device* and listing John L. Faul, Toshihiko Nishimura, Peter N. Kao & Ronald G. Pearl as inventors (the entirety of which is hereby incorporated by reference), we propose creation of an artificial aortocaval fistula as a treatment for COPD, and we disclose the method of creating the fistula and an implantable shunt for maintaining the aortocaval fistula.

Shunts or stents for connecting blood vessels have been proposed for the treatment of coronary artery disease. Makower, *Device, System And Method For Interstitial Transvascular Intervention*, U.S. Pat. No. 6,746,464 (Jun. 8, 2004) (filed Oct. 28, 1998) discloses a stent with a short tubular section spanning the thickness of a coronary artery and an adjacent parallel coronary vein. This stent includes "clovers" on either end of the stent, and these clovers fold radially outwardly to obstruct movement of the stent through the vessel walls. Two clovers on the proximal end of the stent are orthogonal (relative to the radial cross section of the stent) to two clovers on the distal end of the stent, and the interconnecting wires are parallel to the longitudinal axis of the device.

SUMMARY

The devices and methods described below provide for treatment of COPD, hypertension, and left ventricular hypertrophy, and chronic hypoxia. A vascular shunt rivet is disclosed which serves to hold contiguous points of the patient's aorta and inferior vena cava (or other arteries and there associated veins, such as the femoral artery and femoral vein, or the carotid artery and the carotid vein) together and maintain an open flow path from the aorta to the vena cava. The device functions as a rivet, holding the two vessel walls in close proximity, and as a shunt, permitting and maintaining flow from one blood vessel to the other. The device is implanted, between the aorta and inferior vena cava, as a treatment for pulmonary hypertension, COPD and chronic hypoxia.

The shunt rivet is provided in the form of an expandable wire frame structure adapted for transcutaneous delivery and deposit at the desired implantation site. The wire frame structure may be compressed into a small diameter configuration to fit within the distal tip of a delivery catheter. Upon expulsion from the catheter, the wire frame structure resiliently or pseudoelastically expands into a flow-through rivet comprising a tube with expanded heads at either end. When the rivet is released within an artificial fistula formed through the aorta and vena cava walls, it expands to trap the walls between the two expanded heads. The tubular section between the two expanded head may resiliently expand, and may also be balloon-expanded or otherwise plastically deformed to enlarge the flow-through lumen of the tubular section.

DETAILED DESCRIPTION OF THE INVENTIONS

Figure 1:
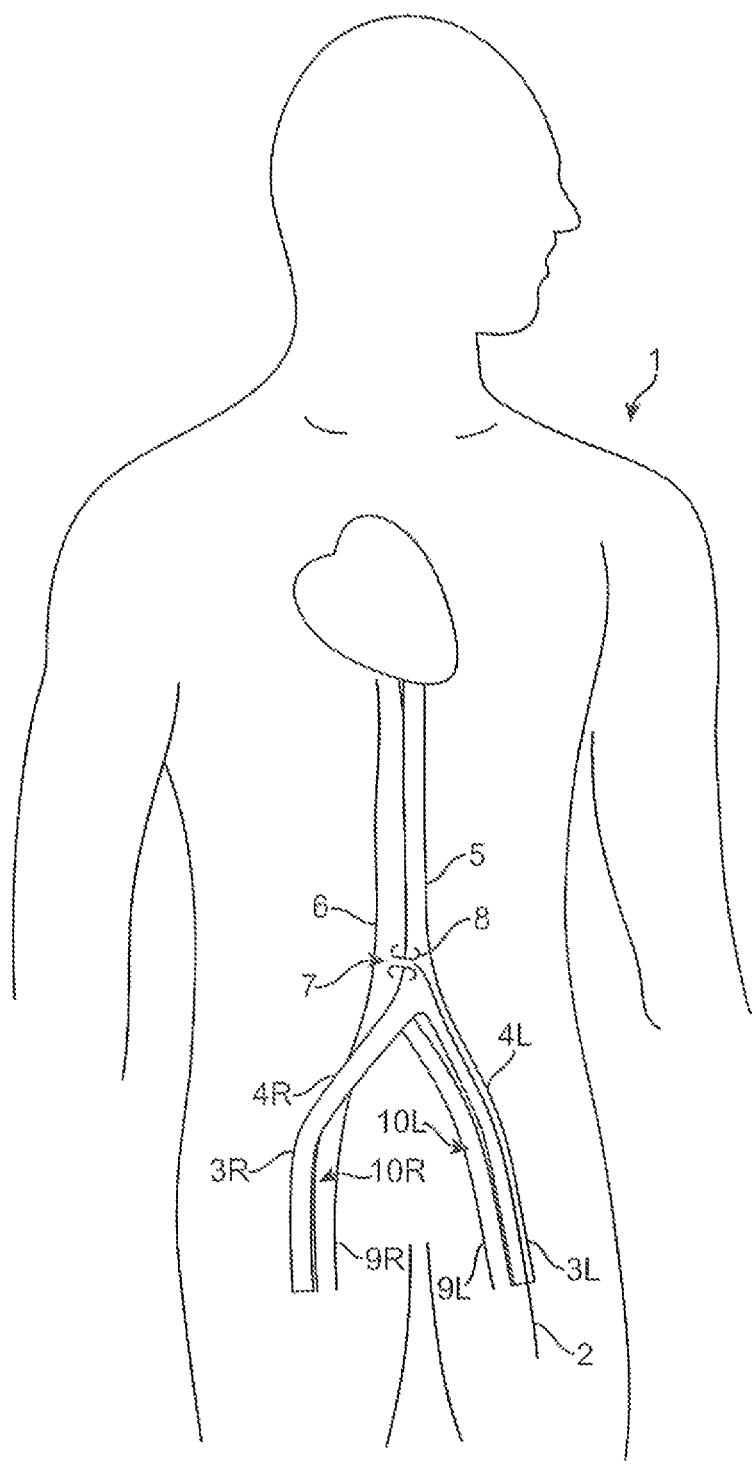
FIG. 1 illustrates the method of installing the shunt rivet to create and maintain an artificial aortocaval fistula.

FIG. 1 illustrates the method of installing the shunt rivet to create and maintain an artificial aortocaval fistula. The patient 1 is shown with a delivery catheter 2 inserted into the left femoral artery/external femoral artery 3L and pushed upwardly through the left common iliac artery 4L to a point just above the aortic/iliac bifurcation in the distal abdominal aorta 5. The inferior vena cava 6 runs parallel to the aorta, and typically is contiguous with the aorta. As shown in the illustration, the left femoral artery provides a nearly straight pathway to a suitable site of the artificial aortocaval fistula 7 within the abdominal aorta (the right femoral vein 9R also provides a straight pathway to the same site on the vena cava side, and may be also be used as an access pathway). The fistula is created by forming a small hole or slit through the walls of both the aorta and the vena cava at immediately adjacent sites, and is maintained by inserting the shunt rivet 8 described below. The device may also be implanted via a route through the left femoral vein 9L, or through the right femoral artery 3R and/or right common iliac artery 4R, though these pathways are not expected to be so readily navigable. The shunt rivet may also be installed in an artificial arterio-venous fistula formed between the femoral vein and femoral artery on either side of the body, indicated as items 10R and 10L, or between the iliac artery and the femoral vein, and at locations in the aorta above the renal arteries.

Figure 2:
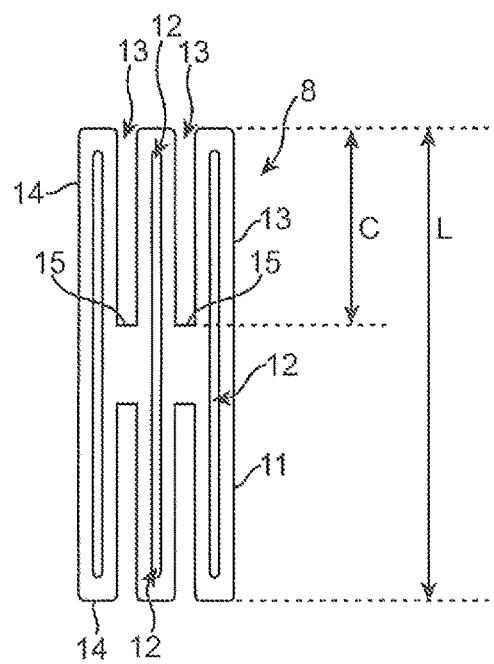
FIG. 2 illustrates an aortocaval shunt rivet in its restrained condition.
Figure 3:
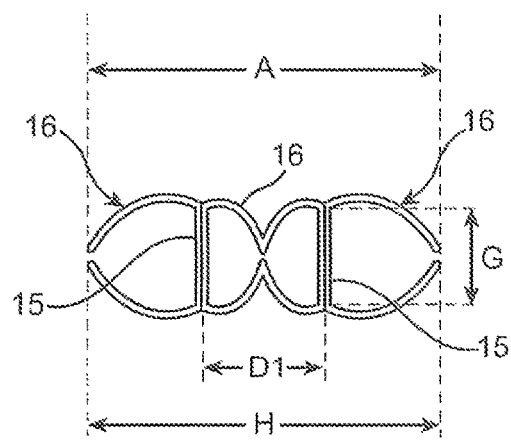
FIG. 3 illustrates the aortocaval shunt rivet of FIG. 2 in a resiliently expanded configuration.

FIG. 2 illustrates the aortocaval shunt rivet 8 in its restrained condition, while FIG. 3 illustrates the aortocaval shunt rivet of FIG. 2 in its resiliently expanded configuration. The shunt rivet may be formed from a single tube 11 of resilient material, such as nitinol, spring steel, glass or carbon composites or polymers, or pseudoelastic (at body temperature) material such as nitinol or comparable alloys and polymers, by laser cutting several closed-ended slots 12 along the length of the tube (leaving the extreme distal and proximal edges of the tube intact) and cutting open-ended slots 13 from the longitudinal center of the tube through the distal and proximal edges of the tube. The open-ended slots are cut between each pair of closed-end slots to form a number of loops 14 joined at the center section by waist segments 15. Though the shunt rivet illustrated in these figures can be made of several loops of wire welded together at the waist section, and many other fabrication techniques, manufacture from a single tube as illustrated has been convenient.

Figure 4:
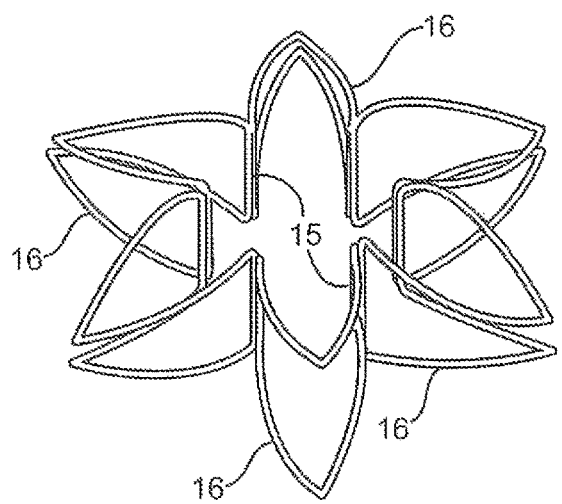
FIG. 4 is a perspective view of the aortocaval shunt rivet of FIG. 2 in a resiliently expanded configuration.

After the tube is cut as described above, it is formed into its eventual resiliently expanded configuration illustrated in FIG. 3. In this configuration, the loops turn radially outwardly from the center section, and evert toward the center plane of the center section, thus forming clinch members 16 in the form of arcuate, everted, petaloid frames at either end of the loop, extending from the generally tubular center section formed by the waist segments 15. For clarity, the term everted is used here to mean that the arc over which the petaloid frame runs is such that the inside surface of the device as configured in FIG. 2 faces radially outwardly from the cylinder established by the tube. FIG. 4 is a perspective view of the shunt rivet in the resiliently expanded configuration illustrated in FIG. 3, more clearly illustrating the relationship between the several petaloid frames at each end of the shunt rivet.

Figure 5:
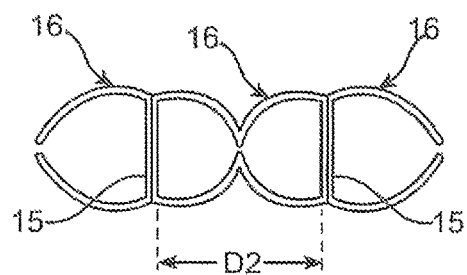
FIG. 5 illustrates the aortocaval shunt rivet of FIG. 2 in a fully expanded configuration.

FIG. 5 shows a side view of the aortocaval shunt rivet of FIG. 2 in a fully expanded configuration. Even after the device has resiliently expanded to the extent possible given its impingement upon the walls of the aorta and the vena cava, the center section may be further expanded by plastic deformation. This may be accomplished by inflating a balloon within the center section, inflating the balloon, and expanding the center section beyond its elastic or superelastic deformation range. By plastically deforming the center section of the shunt rivet, the center section becomes more rigid and able to withstand the compressive force of the walls of the aorta and vena cava.

As illustrated, the construction provides several pairs of longitudinally opposed (that is, they bend to come into close proximity to each other, and perhaps but not necessarily, touch) and aligned (they are disposed along the same longitudinal line) distal and proximal petaloids. Overall, the petaloid frames of the distal section form a "corolla" (analogous to the corolla of a flower) flange or rivet clinch, which impinges on the vena cava wall and prevents expulsion into the aorta, and the petaloid frames of the proximal section form a corolla, flange or rivet clinch (this clinch would be analogous to a rivet head, but it is formed like the clinch after insertion of the rivet), which impinges on the aorta wall and prevents the expulsion of the shunt rivet into the vena cava, and the central section 17 forms a short length of rigid tubing to keep the fistula open. The resilient apposition of the two distal and proximal flanges or corollas so formed will securely hold the shunt rivet in place by resiliently clamping the walls of the aorta and vena cava (even over a considerable range of wall thickness or "grip range").

Referring to FIGS. 2 through 5, the shunt rivet may be manufactured with an overall initial length L of about 8 to 10 mm to obtain a grip range G of about 3 mm (given a typical aortic wall thickness of 2 mm and a typical inferior vena cava wall thickness of 1 mm at the target site), a clinch allowance C of at least about 3 mm (the clinch allowance is the distally protruding portion of a rivet that is turned over, curled or flattened to form the formed head), a formed or blind head allowance A of about 10-16 mm (we use the term blind head to refer to the distal head, which is the head that is formed on the blind side of the joint), a head diameter H of 5-16 mm, an initial shank diameter D1 of 3-8 mm (in the resiliently expanded configuration, prior to plastic deformation), a final shank diameter D2 of 5-12 mm to create a flow through lumen of about 5-10 mm diameter. The grip strength of the shunt rivet should provide for a slight compressive force exerted by the opposing clinch members on the intervening blood vessel walls. Thus, the shunt rivet is formed such that, in the resiliently expanded configuration, produces a grip strength in the range of 0.1 to 1.5 oz (about 3 to 45 gram-force) per clinch member upon the intervening blood vessels of the expected thickness.

Figure 6:
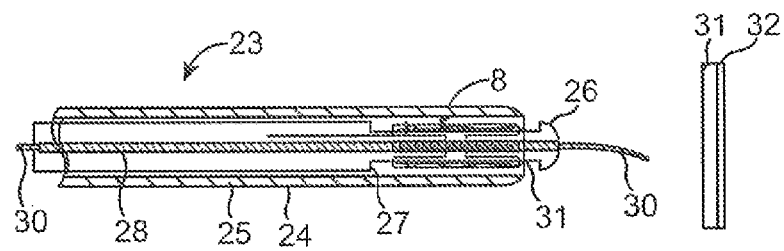
FIGS. 6 through 11 illustrate the deployment of the aortocaval shunt rivet of FIG. 2.

FIGS. 6 through 11 illustrate the method of releasing the shunt rivet so that the distal clinch members are released within the vena cava and the proximal clinch members are released within the aorta. Prior to insertion of the delivery catheter, the surgeon performing the implantation will image the aorta and inferior vena cava with appropriate fluoroscopic, ultrasonic, or other imaging methods, and create a pilot hole in the vessel walls with a crossing catheter. As shown in FIG. 6, the shunt rivet is housed within the distal tip of a delivery catheter 23, and is entirely restrained within the delivery catheter. The delivery catheter includes an outer sheath 24, a shaft 25 which is longitudinally slidable within the outer sheath, and a tapered or rounded tip 26 disposed on the shaft. The tapered may be mounted on a separate shaft, slidably disposed within the shaft 25, so that it may be pushed through the prepared aperture while holding the remainder of the device steady within the aorta. The distal edge of the outer sheath may also be rounded or tapered, as shown. A distally facing shoulder 27 on the shaft, just proximal to the shunt rivet, serves to keep the shunt rivet in place longitudinally as the outer sheath is withdrawn. A guide wire lumen 28 may be provided in the shaft for use with a guide wire 29, and may extend to the proximal end of the shaft for over-the-wire operation or may exit the shaft just proximal to the shunt rivet holding segment for monorail guidewire operation, and other guide wire configurations may also be used. A balloon 30 may be disposed on the shaft (and a suitable balloon inflation lumen provided in the shaft, and a suitable inflation pressure source in fluid communication with the lumen).

Figure 7:
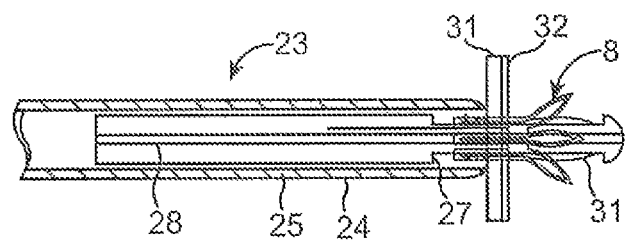
Figure 8:
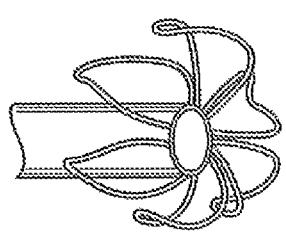

As shown in FIG. 7, the distal tip of the delivery catheter is pushed through a small aperture in the walls of the aorta and vena cava (items 31 and 32) (the aperture is made by the operator, using a separate or integral punch, needle or lance) to create the artificial aortocaval fistula. After the distal tip has entered the vena cava, the outer sheath is pulled proximally to release the distal petaloids, as shown in FIG. 8. After the distal petaloids have reverted to their unrestrained configuration, the entire device is pulled proximally to seat the distal petaloids against the inner wall of the vena cava. Prior to complete release of the shunt rivet, the operator should confirm that its location is acceptable (any suitable imaging technique may be used). To allow retraction in case the shunt rivet must be repositioned, a hook 33 protrudes radially from the shaft 25 and passes through a loop of the shunt rivet. This traps and secures the shunt rivet within the outer sheath 24 until the outer sheath is moved proximally to release the proximal clinch members, so that the operator may pull the shunt rivet back into the outer sheath in case its location, as visualized prior to complete release of the shunt rivet, is undesirable. Any other retaining means, such as a resilient or spring-loaded detent, a retractable pawl which engages a loop of the shunt rivet, of a retractable hook extending inwardly from the outer sheath, may be used in place of the illustrated hook.

Figure 9:
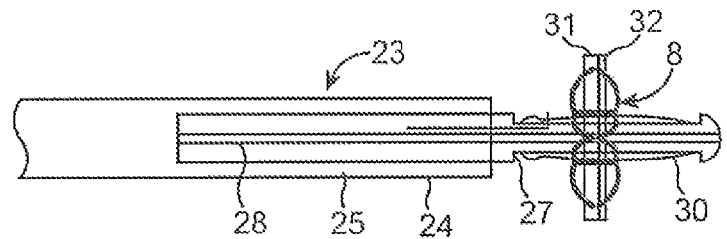
Figure 10:
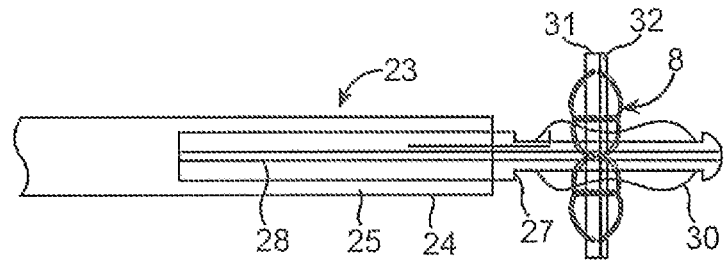
Figure 11:
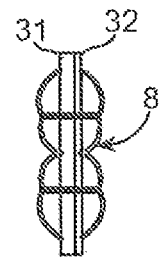

Then the outer sheath is pulled further proximally to release the proximal petaloids, as shown in FIG. 9. With the shunt rivet securely set in the artificial fistula, the center section may then be expanded by inflating the balloon as shown in FIG. 10. Upon withdrawal of the shaft, the shunt rivet remains in place to hold the two perforations in the blood vessel wall in apposition to each other to maintain the fistula, and to maintain an open shunt pathway between the aorta and vena cava, as shown in FIG. 11.

The final form of the shunt rivet is, according to the above description, accomplished with the method that includes forming the generally tubular structure having a central section with a first diameter, a proximal clinch section defined by one or more clinch members, and a distal clinch section defined by one or more clinch members, training the proximal and distal clinch members to make them resiliently biased to bend radially outwardly from the central section; then resiliently compressing the tubular structure to maintain a generally tubular shape and restraining the compressed tubular structure in a compressed configuration suitable for percutaneous insertion into the body; inserting the structure through apposing apertures in the aorta wall and vena cava wall of a patient such that the distal clinch members protrude into the vena cava of the patient and the central section is disposed within the apertures; and then releasing the distal clinch members to permit resilient expansion of the distal clinch members followed by expanding the central section through plastic deformation to larger diameter and releasing the proximal clinch members to permit resilient expansion of the proximal clinch members (the proximal clinch members may be released before or after expansion of the central section).

Figure 12:
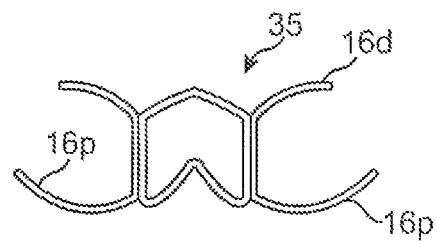
FIG. 12 illustrates an aortocaval shunt rivet with asymmetrically shaped distal and proximal flanges.
Figure 13:
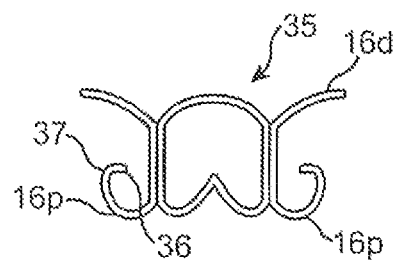
FIG. 13 illustrates an aortocaval shunt rivet with asymmetrically shaped distal and proximal flanges.

The shunt rivet illustrated above may be modified as shown in FIGS. 12 and 13, which show an aortocaval shunt rivet with asymmetrically shaped distal and proximal flanges. In FIG. 12, the shunt rivet 35 is similar to the shunt rivet of FIGS. 2 through 4, and includes the central section, the distal flange comprised of multiple petaloid wire-frame members 16*d*, and the proximal flange comprised of multiple petaloid wire-frame members 16*d*. In this embodiment, the distal corolla is horn-shaped, "salverform" or "funnelform" (as those terms are used in botany), with the petaloids arcing outwardly without everting (without a substantial arc in the proximal direction), while the proximal corolla is perianth-like, arcing outwardly and everting with a substantial arc in the distal direction. Each petaloid is significantly reflexed, like the perianth of a narcissus cyclamineus. FIG. 13 illustrates another embodiment of the aortocaval shunt rivet with asymmetrically shaped distal and proximal flanges. In FIG. 13, the proximal petaloids are highly reflexed, and evert to form pigtails with an arc of over 180°, and preferably, as illustrated, an arc in excess of about 270°, such that the proximal petaloids bend radially inwardly toward the tips 36 to present a length of wire 37, rather than the tip of the petaloids, for impingement on the blood vessel wall. One or both of the distal or proximal petaloids/clinch members may be modified to form the pigtails illustrated in FIG. 13. In the embodiments shown, the petaloids are gamopetalous (with the petals united by their margins, at least at the base, as in FIG. 2 et seq.), but they may also be polypetalous as shown below FIGS. 14, 15 and 16. The embodiments shows are also actinomorphic, though they may be constructed in zygomorphic fashion with asymmetrical petaloids.

Figure 14:
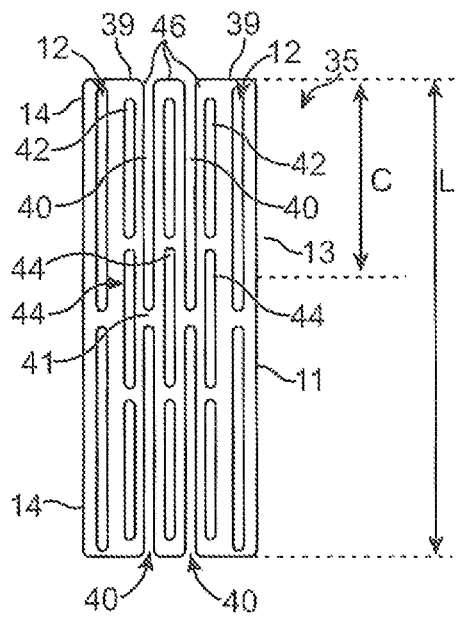
FIGS. 14, 15 and 16 illustrate an aortocaval shunt rivet with strut members that form diamond-shaped cells in the central section upon expansion.
Figure 15:
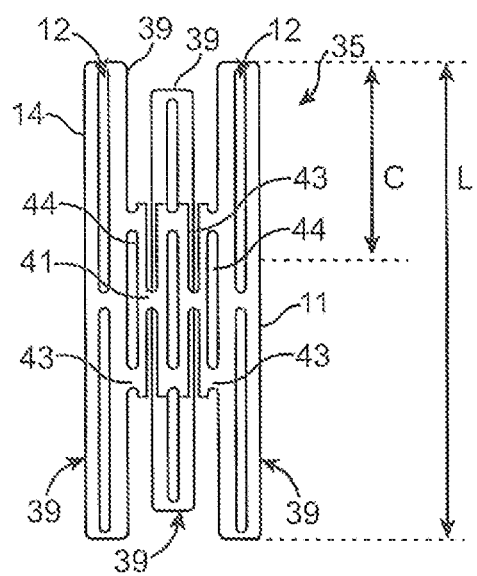
Figure 16:
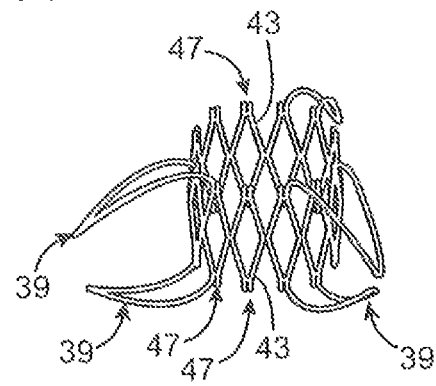

FIGS. 14, 15 and 16 illustrate an aortocaval shunt rivet 8 with diamond shaped strut members in the central section. This shunt rivet provides a central section 17 with a series of expandable loops joined by circumferentially oriented struts 38. FIG. 14 illustrates a tube 11 with numerous slots cut into it to form the shunt rivet shown in FIG. 16. Slots 12 are closed-end slots, leaving a loop 14 extending from the central section 17 to form a clinch member cell 39. Slots 40 are open or closed-end slots extending from the center of the device, leaving small circumferential struts 41 connecting adjacent cells of the device. Slots 42 are open or closed-end slots extending from the center section of the device, leaving larger waist sections 43 connecting the circumferential struts with adjacent clinch member cells of the device. Slots 44 are closed-end slots extending through the waist sections. As shown in FIG. 15, some waste area (segments intended to be removed) 46 shown in FIG. 14 are cut away and discarded, leaving expandable waist section cells 47 and clinch cells 39, interconnected by the circumferential struts 38. Though the device is illustrated with three clinch members on each end, the number of clinch members formed in the shunt rivet may be varied. The waist section cells and clinch member cells, can, as shown at 48, share struts which define contiguous cells. As shown in FIG. 16 the waist section cells, when expanded, form the diamond shaped cells of the central section. The clinch member cells comprise petaloid cells which may be described as lanceolate (narrow and tapering to an apex (though the apex is preferably blunt)), or ovate (having a broad base and narrow tip) rather than reniform or orbicular. The tip of the petaloid is preferably obtuse, rounded or blunt. As can be appreciated from FIG. 16 the clinch members may also be described as longitudinally extending wires which connect the longitudinally tips of adjacent waist section cells.

Figure 17:
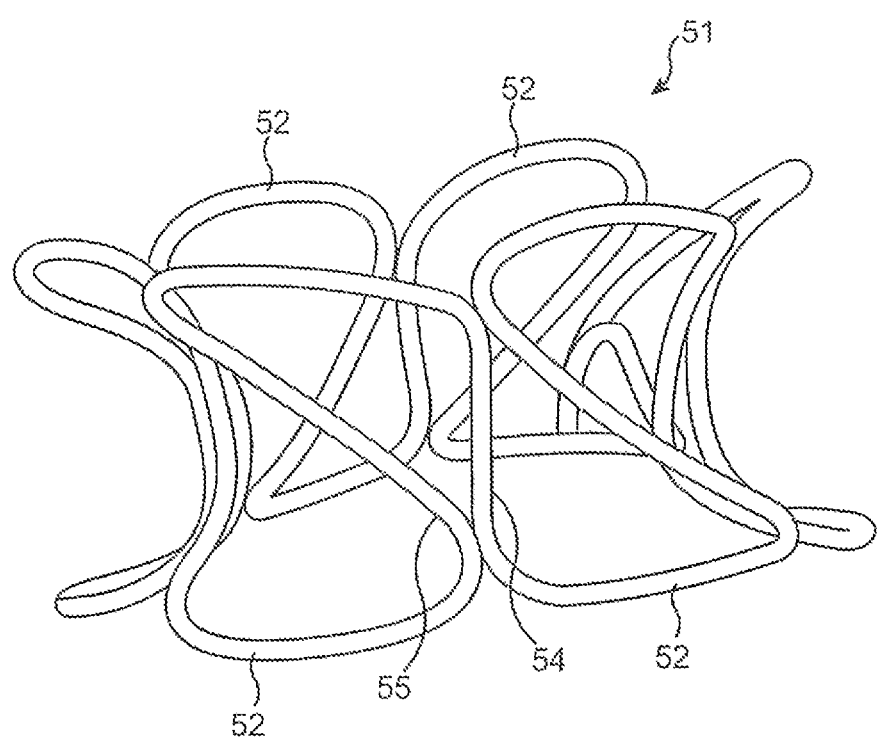
FIGS. 17 and 18 illustrates an aortocaval shunt rivet formed with a single wired wrapped to form the device.
Figure 18:
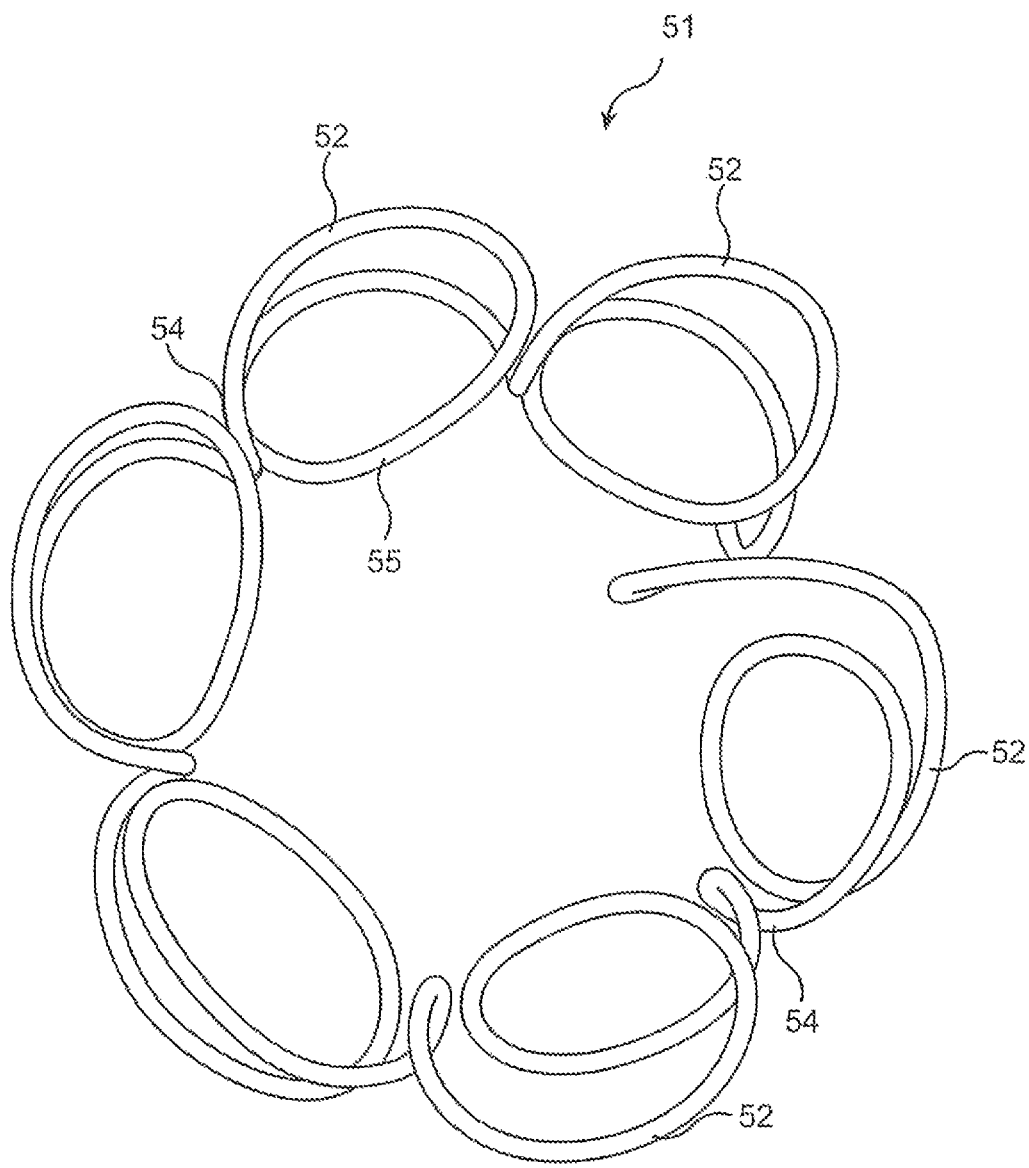

FIGS. 17 and 18 illustrate an aortocaval shunt rivet 51 formed with a single wired wrapped to form the device. In this device, a single wire has been wrapped around a specially formed mandrel to form a number of clinch members 52 on one end of the device and a number of clinch members 53 on the other end of the device. As illustrated, each clinch member is slanted relative to the radius of the device, and the wires forming the waist segment of the device are also oblique to the longitude of the device. As viewed from the top, each cinch member comprises a substantially circular arc, and the wire continues from the arc longitudinally toward the opposite end of the device, forming straight waist segment 54 where it runs substantially parallel to the long axis of the device until it arcs circumferentially away from the previous arc to form the clinch member on the opposite end, whereafter it loops around to extend retrograde relative to the circumference, forming waist segment 55 running obliquely relative to the long axis, and back toward the first end of the device until it curves again circumferentially forward to form the loop of the next clinch member circumferentially adjacent the first loop and longitudinally in line with the immediate previously formed clinch member on the opposite end of the shunt rivet, and continues in this fashion until the entire tubular structure of the device is achieved. In tracing its path, the wire may cross over one or more other portions of the wire.

Figure 19:
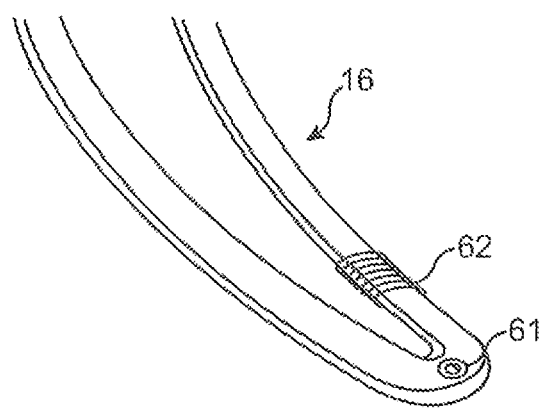
FIG. 19 shows a detail of the clinch member, illustrating radiopaque markers on the shunt rivet.

FIG. 19 shows a detail of the clinch member, illustrating radiopaque markers on the shunt rivet. A radiopaque marker may be provided in the form of a radiopaque rivet 61 disposed near the tip of the clinch member 16, or it may be provided in the form of a wrapped coil of radiopaque wire or thread 62. The radiopaque markers may be comprised of platinum, iridium, tantalum, barium sulfate or other radiopaque materials. Similar markers may also be applied to the waist section. The marker material may also be selected to enhance visibility under ultrasound imaging, magnetic resonance imaging, or other suitable imaging techniques.

Figure 21:
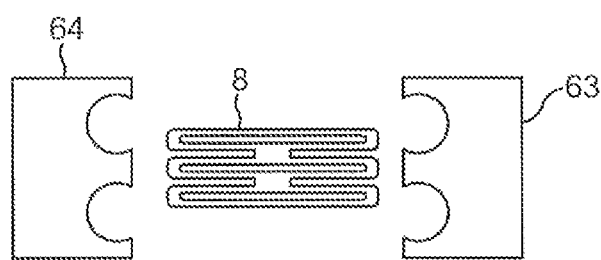
FIGS. 20 and 21 illustrates a mandrel useful for forming and training/heat setting the shunt rivets.
Figure 20:
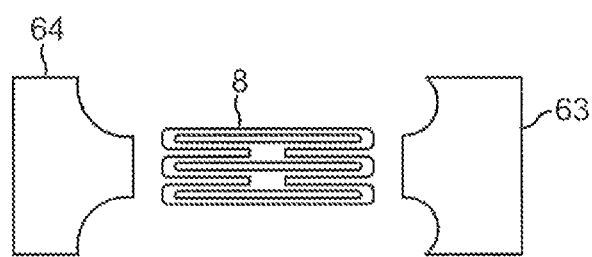

FIGS. 20 and 21 illustrate mandrels or dies useful for forming and training/heat setting the shunt rivets. As shown in FIG. 20, a two-part mandrel comprises a distal mandrel portion 63 and a proximal mandrel portion 64. Each mandrel is shaped to correspond to the desired final shape of the shunt rivet and its clinch members. The mandrel portions are inserted into the tube, after it has been cut, so as to deform the device. Where the device is formed from a pseudoelastic material that must be heat set or trained, the mandrels are dimensioned to deform the device to its desired open configuration. Where the device is formed of spring steel or the like, the mandrel is dimensioned to bend the clinch members beyond the desired final configuration. Thus, the mandrel of FIG. 20 and the mandrel of FIG. 21, though shaped differently, may be used to form quite similar shapes for devices made of nitinol and spring steel. The mandrel shapes may be modified as desired to achieve various clinch member shapes, such as the asymmetrical shapes shown in FIGS. 12 and 13.

Figure 22:
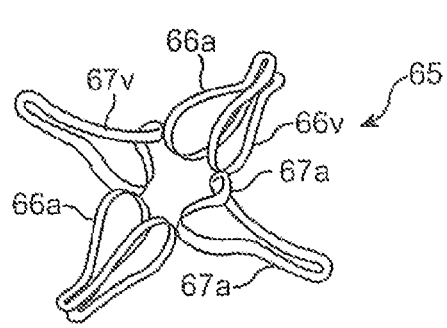
FIG. 22 is a perspective view of a shunt rivet in which the clinch members are biased to provide a pair of clinch members biased to close upon contiguous parallel portions of adjacent vessels while exerting slight pressure on circumferentially spaced points on the side walls of the adjacent blood vessels.

The shunt rivet may be modified as shown in FIGS. 22 through 25. FIG. 22 is a perspective view of a shunt rivet 65 in which the clinch members are biased to provide pairs of clinch members 66*a* and 66*v* biased to close upon contiguous parallel portions of adjacent vessels and a pair of clinch members 67*a* and 67*v* biased to exert slight pressure, and establish slight compliance mismatch, on circumferentially spaced points on the side walls of the adjacent blood vessels. Each clinch member is slit down the center to allow radially expansion of the device through radial deformation of the clinch member.

Figure 23:
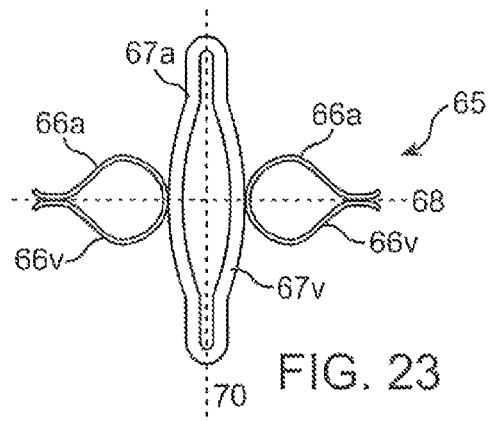
FIG. 23 is a side view of the shunt rivet 22 showing the substantial closure of longitudinally oriented clinch members.
Figure 24:
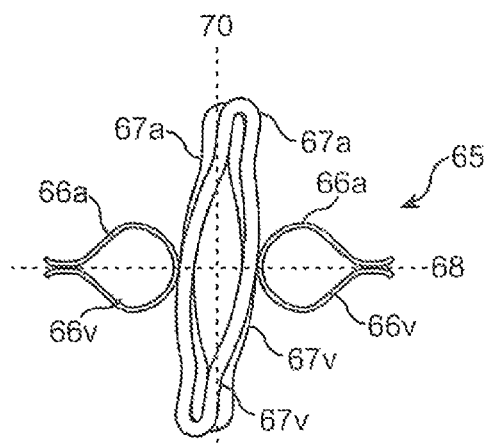
FIG. 24 is a side view of the shunt rivet 22 showing the preferred angle of the transversely oriented clinch members relative to the axis of the device.

FIG. 23 is a side view of a shunt rivet of FIG. 22 showing the substantial closure of longitudinally oriented clinch members 66*a* and 66*v*. These clinch members are formed to evert, such that the tips of opposing clinch members 66*a* and 66*v* are closely proximate each other when released (in the expanded configuration shown). A short segment at the distal tip of each clinch member is turned away from the transverse midline 68 of the device to form an atraumatic bearing surface for impingement on the blood vessels walls. As illustrated, the clinch members 66*a* and 66*v* comprise a continuously formed clip, with no intervening waist segment between the arterial portion of the clip and the venous portion of the clip. The clip resembles a tool clip, as that term is used in other arts. Preferably the clinch members making up the tool clip are joined directly together, without an intervening rectilinear base (though a rectilinear base may be incorporated if desired to accommodate the anatomy of the arterio-venous fistula in a particular site), to create a smoothly arcuate transition from the distal clinch member to the proximal clinch member. FIG. 24 is a side view of the shunt rivet 22 showing the preferred angle of the transversely oriented clinch members 67*a* and 67*v* relative to the axis 70 of the device. In this embodiment, the transversely oriented clinch members 67*a* and 67*v* (both the near and far pairs are visible in this view) are set at a small angle from axis 70. In the unrestrained configuration, the clinch members 67*a* on the arterial side of the device (typically the first side of the device to be released from the catheter given the preference for transvenous delivery) are inclined toward the upstream or retrograde direction. Clinch members 67*v* on the venous side of the device are inclined toward the upstream or retrograde direction within the vein. This configuration facilitates release of the device from the small delivery catheter used to insert it into a fistula.

Figure 25:
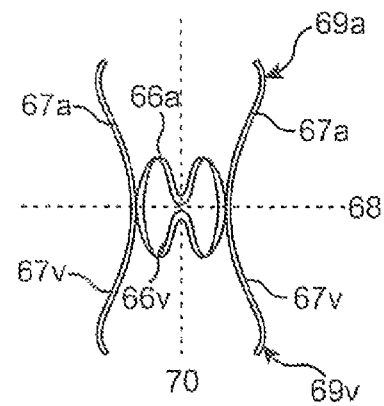
FIG. 25 is a side view of the shunt rivet of FIG. 22 showing transversely oriented clinches.

FIG. 25 is a side view of the shunt rivet of FIGS. 22 through 24 showing transversely oriented clinch members 67*a* and 67*b* with substantial spacing between the tips of the clinch members (in the expanded configuration shown). Also, clinch members 67*a* and 67*b* constitute a continuously formed tension spring (shaped substantially like the tension spring used in window frames, having an arcuate or bow shape, with the ends arcing outwardly from the axial centerline 70 of the device and adapted to impinge upon or exert force on the blood vessels and the middle of the arch adapted to exert force on the remainder of the shunt rivet to which it is fixed), with no intervening waist segment between the arterial portion of the tension spring and the venous portion of the tension spring, and the tension spring formed to impinge on the sidewall of the artery or vein at a point circumferentially displaced from the center of the rivet without deforming the artery and/or vein walls to bring the opposite tips 69*a* and 69*v* into apposition such as that achieved by the tips of the tool clips. A short segment at the distal tip of each clinch member is turned away from the axial centerline 70 of the device to form an atraumatic bearing surface for impingement on the blood vessel walls.

The device may thus be described, in their open and unconstrained conditions, as comprising two parallel tool clips secured at their closed ends to two parallel tension springs, at the midpoints of the tension springs, to create an orthogonal or cruciform grouping of alternating spring clips and tension springs. Adopting the botanical language used for other embodiments, each side of the device comprises a pair of petaloids arcing outwardly from the axial centerline of the device without everting (without a substantial arc in the proximal direction), and a pair of petaloids arcing outwardly and everting with a substantial arc in the distal direction, with corresponding petaloid structures being joined at their proximal ends without an intervening waist segment. Each petaloid is formed in an open frame V-shape. Though illustrated with a pair of clips and a pair of tension springs, the device may be formed with additional tension springs or clips, as dictated by the local anatomy of a particular installation. In appropriate anatomical conditions, the device may comprise four clips in the tool clip configuration, or the comparable everting petaloid pairs (in which all clinch members evert substantially to close upon the vessel wall), arranged orthogonally, where the tool clips are arranged in a circular arrangement with the closed end of each clip being secured to the closed and of an adjacent clip, such that the open end of each tool clip is directed outwardly from the circular arrangement. The device may also include additional arcuate tension springs and/or tool clip portions, thus departing from the cruciform configuration shown while achieving the benefit of substantial spacing of the vessel contacting tips from the arterio-venous fistula.

Figure 26:
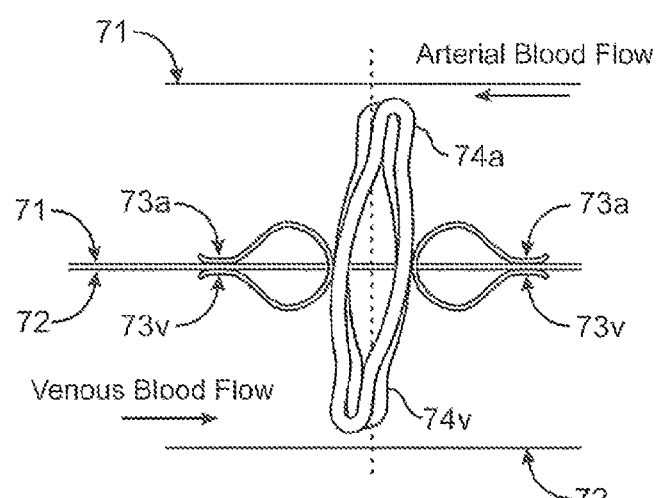
FIG. 26 shows the shunt rivet of FIGS. 22 through 25 installed between an artery and a vein, illustrating the construction of the device relative to the environment of use.

FIG. 26 shows the shunt rivet of FIGS. 22 through 25 installed between an artery 71 and vein 72, in order to illustrate the construction of the device relative to the environment of use. The tips of the "tool clip" portion of the device (66*a* and 66*b*) close upon points in the respective vessels 73*a* and 73*v* which are longitudinally spaced (relative to the blood vessels) from the arterio-venous fistula formed in which the device is placed. The points of impingement are significantly spaced from the fistula, as illustrated. The tips of the tension spring portion (67*a* and 67*v*) of the device impinge on circumferentially spaced points 74*a* and 74*v*. As shown in FIG. 26, the circumferential points of impingement are significantly spaced from the fistula. The circumferential spacing is preferably 30° to 90°, but may be adjusted to fit local anatomy. In this manner, the shunt rivet avoids engagement of the blood vessels adjacent the fistula. As shown in FIG. 26, the ultimate shape of the installed shunt rivet may vary from the unrestrained shape due to the remaining constraint of the blood vessel walls, though the device is biased to resiliently or superelastically return to the unrestrained shapes of FIGS. 22 through 25. After installation, the shunt rivet holds the adjacent artery and vein together and maintains an open flow path through opening defined by the roughly circular arrangement of the clips and tension springs. Should the arrangement appear to be somewhat squared or angular, pentagonal, hexagonal, etc., given the particular geometries of the various parts, it is intended that such departures from perfect circular arrangement be included under the description of a circular arrangement.

The devices described above may be provided with coatings or additional structures which serve as matrices for various therapeutic compounds. Drug eluting coatings, additional drug eluting strut members, drug eluting membranes surrounding the central section or drug eluting masses filling the cells of the device may be added to the devices. For the aortocaval application and the arterio-venous application, therapeutic agents such as heparin and other anti-coagulants and paclitaxol, rapamycin (Sirolumis™), everolimus and other anti-stenotic compounds can be applied to the stent in polymer matrices which permit elution of these drugs over a period of time ranging from several hours to several months after implantation. Polymers such as polyurethane can be used as the matrix.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. An intravascular connector comprising:

a first pair of clinch members having a deployed configuration disposed along a first midline and along adjacent parallel portions of a first vessel and a second vessel, wherein the first pair of clinch members are biased to evert and close upon apposed adjacent parallel portions of the first and second vessels such that a distal portion of each of the first pair of clinch members is biased to close upon the apposed adjacent parallel portions of the first and second vessels when the first pair of clinch members are released in their deployed configuration, wherein the first pair of clinch members are biased to close upon the apposed adjacent parallel portions of the first and second vessels such that the distal portion of each of the first pair of clinch members is proximate to one another when the first pair of clinch members are released in their deployed configuration, and wherein a first part of the distal portion of each of the first pair of clinch members extends towards the first midline of the connector, and wherein a second part of the distal portion of each of the first pair of clinch members extends away from one another and away from the first midline of the connector; and a second pair of clinch members having a deployed configuration disposed along a second midline transverse to the first midline, wherein the second pair of clinch members are configured to extend in opposing directions along the second midline and away from the first midline, wherein the second midline is configured to be transverse relative to a longitudinal direction of the first and second vessels, wherein a distal portion of each of the second pair of clinch members extends from a portion fixed to the connector such that the distal portion of each of the second pair of clinch members is spaced apart from one another, wherein the second pair of clinch members extend in an arcuate shape relative to the portion fixed to the connector such that the distal portion of each of the second pair of clinch members is biased to exert a pressure on a circumferentially spaced point that is displaced from the connector on a side wall of the first or second vessel, wherein the distal portion of each of the first pair of clinch members forms an atraumatic bearing surface therebetween for impingement on the first and second vessels, and wherein the distal portion of each of the second pair of clinch members forms an atraumatic bearing surface for impingement on the first or second vessel, wherein the first pair of clinch members extend along the first midline in an arcuate shape, and wherein the second pair of clinch members extend along the second midline in an arcuate shape, wherein the arcuate shape of each of the first pair of clinch members defines a first concavity and a second concavity when viewed from a first side of the connector, wherein the first concavities face toward each other and toward the first midline, and wherein the second concavities face away from each other and away from the first midline, wherein the arcuate shape of each of the second pair of clinch members defines a third concavity when viewed from a second side of the connector, and wherein the third concavities face toward each other and toward the second midline, wherein a base of each of the first pair of clinch members and the distal portion of each of the first pair of clinch members are proximate the first midline, and wherein a base of each of the second pair of clinch members is proximate one of the bases of the first pair of clinch members, and wherein the distal portion of each of the first pair of clinch members is biased to close toward the first midline, and wherein the distal portion of each of the second pair of clinch members is biased to exert pressure away from the second midline.

2. The connector of claim 1 wherein each clinch member defines a slit therealong about which radial deformation of the clinch members occurs when the connector is radially expanded.

3. The connector of claim 1 wherein the first pair of clinch members comprise a continuously formed clip absent an intervening waist segment.

4. The connector of claim 1 wherein the second pair of clinch members defines an angle relative to the first pair of clinch members.

5. The connector of claim 1 wherein the clinch members of the first and second pair when disposed within an artery are configured to be inclined towards an upstream or retrograde direction within the artery.

6. The connector of claim 1 wherein the clinch members of the first and second pair when disposed within a vein are configured to be inclined towards an upstream or retrograde direction within the vein.

7. The connector of claim 1 wherein the second pair of clinch members are biased to establish a slight compliance mismatch between the first and second vessels.

8. The connector of claim 1 wherein the distal portion of each of the second pair of clinch members is spaced apart from one another when the clinch members of the second pair are released in their deployed configuration.

9. The connector of claim 1 wherein the second pair of clinch members comprise a continuously formed clip absent an intervening waist segment.

10. The connector of claim 9 wherein the distal portion of each of the second pair of clinch members arc outwardly relative to the second midline.

11. The connector of claim 1 further comprising a therapeutic drug coating or membrane at least partially covering the connector.

12. The connector of claim 1 wherein the second pair of clinch members comprise bow-shaped wire clips.

13. An intravascular connector comprising:

a pair of clips having a deployed configuration disposed along a first midline and along adjacent parallel portions of a first vessel and a second vessel, wherein the pair of clips are biased to evert and close upon apposed adjacent parallel portions of the first and second vessels such that a distal portion of each of the pair of clips is proximate to one another when the pair of clips are released in their deployed configuration, and wherein a first part of the distal portion of each of the pair of clips extends towards the first midline of the connector, and wherein a second part of the distal portion of each of the pair of clips extends away from one another and away from the first midline of the connector; and a pair of tension springs having a deployed configuration disposed along a second midline transverse to the first midline, wherein the pair of tension springs are configured to extend in opposing directions along the second midline and away from the fir midline, wherein the second midline is configured to be transverse relative to a longitudinal direction of the first and second vessels, wherein a distal portion of each of the pair of tension springs extends from a portion fixed to the connector such that the distal portion of each of the pair of tension springs is spaced apart from one another, wherein the pair of tension springs extend in an arcuate shape relative to the portion fixed to the connector such that the distal portion of each of the pair of tension springs is configured to be positioned on a circumferentially spaced point on a side wall of the first or second vessel, wherein an arrangement of the pair of clips and the pair of tension springs define an opening therebetween such that an open flow path is maintained between the first and second vessels, wherein the distal portion of each of the pair of clips forms an atraumatic bearing surface therebetween for impingement on the first and second vessels, and wherein the distal portion of each of the pair of tension springs forms an atraumatic bearing surface for impingement on the first or second vessel, wherein the pair of clips extend along the first midline in an arcuate shape, and wherein the pair of tension springs extend along the second midline in an arcuate shape, wherein the arcuate shape of each of the pair of clips defines a first concavity and a second concavity when viewed from a first side of the connector, wherein the first concavities face toward each other and toward the first midline, and wherein the second concavities face away from each other and away from the first midline, wherein the arcuate shape of each of the pair of tension springs defines a third concavity when viewed from a second side of the connector, and wherein the third concavities face toward each other and toward the second midline, wherein a base of each of the pair of clips and the distal portion of each of the pair of clips are proximate the first midline, and wherein a base of each of the pair of tension springs is proximate one of the bases of the pair of clips, and wherein the distal portion of each of the pair of clips is biased to close toward the first midline, and wherein the distal portion of each of the pair of tension springs is biased to exert pressure away from the second midline.

14. The connector of claim 13 wherein the clips are comprised of a continuously formed member absent an intervening waist segment.

15. The connector of claim 14, wherein the tension springs are comprised of a continuously formed member absent an intervening waist segment.

16. The connector of claim 13 wherein the distal portion of each of the pair of tension springs is biased to exert a pressure on a circumferentially spaced point on a side wall of the first or second vessel.

17. The connector of claim 13 wherein the connector comprises at least two pairs of clips positioned outwardly relative to one another.

18. The connector of claim 17 further comprising at least two pairs of tension springs positioned outwardly relative to one another.

19. The connector of claim 18 wherein the pairs of clips and pairs of tension springs are positioned in a circular arrangement with a closed end of each clip or tension spring being secured to a closed end of an adjacent clip or tension spring such that an open end of each clip or tension spring is directed outwardly from the circular arrangement.

20. The connector of claim 19 wherein the pairs of clips and pairs of tension springs are arranged in an alternating manner.

21. The connector of claim 19 wherein the pairs of clips and pairs of tension springs are circumferentially spaced between 30 to 90 degrees from one another in the circular arrangement.

22. The connector of claim 13 wherein the distal portion of each of the pair of clip is configured to close upon a point positioned away from the opening along the first midline.

23. The connector of claim 13 further comprising a therapeutic drug coating or membrane at least partially covering the connector.

24. The connector of claim 13 wherein the pair of tension springs comprise bow-shaped wire clips.

* * * * *